US007695528B2

(12) United States Patent
Lang et al.

(10) Patent No.: US 7,695,528 B2
(45) Date of Patent: *Apr. 13, 2010

(54) CALCIUM CARBONATE GRANULATION

(75) Inventors: Kevin W. Lang, Lloyd Neck, NY (US); Raya Levin, Langhorne, PA (US); James W. Dibble, Port Jefferson, NY (US); Gregory B. Murphy, Sands Point, NY (US)

(73) Assignee: Delavau LLC, Philadelphia, PA (US)

( * ) Notice: Subject to any disclaimer, the term of this patent is extended or adjusted under 35 U.S.C. 154(b) by 574 days.

This patent is subject to a terminal disclaimer.

(21) Appl. No.: 11/675,459

(22) Filed: Feb. 15, 2007

(65) Prior Publication Data

US 2007/0178154 A1 Aug. 2, 2007

Related U.S. Application Data

(63) Continuation of application No. 10/631,923, filed on Jul. 31, 2003, now Pat. No. 7,198,653.

(51) Int. Cl.
*B01J 2/00* (2006.01)

(52) U.S. Cl. .................. 23/313 R; 423/430; 424/465; 426/443; 426/648

(58) Field of Classification Search ............... 23/313 R; 423/430; 424/465; 426/443, 648
See application file for complete search history.

(56) References Cited

U.S. PATENT DOCUMENTS

| | | | |
|---|---|---|---|
| 3,627,583 A | 12/1971 | Troy et al. | |
| 3,639,168 A | 2/1972 | Monti et al. | |
| 3,639,169 A | 2/1972 | Broeg et al. | |
| 3,646,689 A | 3/1972 | Kuchenthal et al. | |
| 3,843,778 A | 10/1974 | Diamond et al. | |
| 3,933,670 A | 1/1976 | Brill et al. | |
| 3,969,546 A | 7/1976 | Saeman | |
| 4,051,222 A | 9/1977 | Gnyra | |
| 4,054,631 A | 10/1977 | Mori et al. | |
| 4,071,304 A | 1/1978 | Chauvin et al. | |
| 4,140,760 A | 2/1979 | Withington | |
| 4,170,658 A * | 10/1979 | Skinner et al. | 423/430 |
| 4,183,738 A | 1/1980 | Carmon | |
| 4,230,693 A | 10/1980 | Izzo et al. | |
| 4,257,817 A | 3/1981 | Mathur et al. | |
| 4,339,428 A | 7/1982 | Tencza | |
| 4,409,016 A | 10/1983 | Mutsers et al. | |
| 4,446,135 A | 5/1984 | Fountaine | |
| 4,486,412 A | 12/1984 | Shah et al. | |
| 4,533,543 A | 8/1985 | Morris et al. | |
| 4,540,584 A | 9/1985 | Someya | |
| 4,582,615 A | 4/1986 | Ramachandran et al. | |
| 4,609,473 A | 9/1986 | Ramachandran et al. | |
| 4,609,543 A | 9/1986 | Morris et al. | |
| 4,650,669 A | 3/1987 | Alexander et al. | |
| 4,656,028 A | 4/1987 | Cuca | |
| 4,664,915 A | 5/1987 | Simonian | |
| 4,678,661 A | 7/1987 | Gergely et al. | |
| 4,711,748 A | 12/1987 | Irwin et al. | |
| 4,744,987 A | 5/1988 | Mehra et al. | |
| 4,746,445 A | 5/1988 | Weinstein | |
| 4,772,467 A | 9/1988 | Pak | |
| 4,812,303 A | 3/1989 | Iorio | |
| 4,828,820 A | 5/1989 | Glass et al. | |
| 4,851,137 A | 7/1989 | Weinstein | |
| 4,861,590 A | 8/1989 | Grodberg | |
| 4,866,023 A | 9/1989 | Ritter et al. | |
| 4,867,977 A | 9/1989 | Gailly et al. | |
| 4,883,788 A | 11/1989 | Day et al. | |
| 4,889,725 A | 12/1989 | Veltman | |
| 4,946,679 A | 8/1990 | Thys-Jacobs | |
| 4,954,134 A | 9/1990 | Harrison et al. | |
| 5,002,777 A | 3/1991 | Cuca | |
| 5,173,305 A | 12/1992 | Grimberg | |
| 5,228,895 A | 7/1993 | Kelly et al. | |
| 5,302,396 A | 4/1994 | Phadke et al. | |
| 5,362,688 A | 11/1994 | Porta et al. | |
| 5,366,513 A | 11/1994 | Goldmann et al. | |
| 5,429,825 A | 7/1995 | Reo et al. | |
| 5,443,850 A | 8/1995 | Thys-Jacobs | |
| 5,455,050 A | 10/1995 | Beyerle et al. | |

(Continued)

FOREIGN PATENT DOCUMENTS

EP 0439373 7/1991

(Continued)

OTHER PUBLICATIONS

"OMAYA-CAL FG-15 AZ Specification Production (Omaya Arizona, Inc)," Nov. 2, 2001, http://ccicalifornia.com/pdf/caciumcarb/fg15_specs.pdf.

(Continued)

*Primary Examiner*—Stuart Hendrickson
(74) *Attorney, Agent, or Firm*—Jonathan D. Ball; King & Spalding LLP

(57) ABSTRACT

Highly compactable granulations and methods for preparing highly compactable granulations are disclosed. More particularly, highly compactable calcium carbonate granulations are disclosed. The granulations comprise powdered materials such as calcium carbonate that have small median particle sizes. The disclosed granulations are useful in pharmaceutical and nutraceutical tableting and provide smaller tablet sizes upon compression than previously available.

19 Claims, No Drawings

U.S. PATENT DOCUMENTS

| | | | |
|---|---|---|---|
| 5,536,432 | A | 7/1996 | Cicciari et al. |
| 5,571,334 | A | 11/1996 | Dunn et al. |
| 5,603,979 | A | 2/1997 | Ladson et al. |
| 5,629,013 | A | 5/1997 | Upson et al. |
| 5,635,208 | A | 6/1997 | Parekh et al. |
| 5,637,313 | A | 6/1997 | Chau et al. |
| 5,665,692 | A | 9/1997 | Kaminsky |
| 5,743,934 | A | 4/1998 | Wommack et al. |
| 5,747,067 | A | 5/1998 | Auguello et al. |
| 5,807,580 | A | 9/1998 | Luber |
| 5,858,413 | A | 1/1999 | Jettka et al. |
| 5,874,065 | A | 2/1999 | Pardini |
| 5,914,135 | A | 6/1999 | Dubek et al. |
| 5,919,491 | A | 7/1999 | Adusumilli et al. |
| 5,922,704 | A | 7/1999 | Bland |
| 5,929,021 | A | 7/1999 | Dhanuka et al. |
| 5,942,255 | A | 8/1999 | Klesges |
| 5,997,599 | A | 12/1999 | Wommack et al. |
| 6,056,905 | A | 5/2000 | Akkermans et al. |
| 6,066,342 | A | 5/2000 | Gurol et al. |
| 6,077,820 | A | 6/2000 | Dhanuka et al. |
| 6,103,274 | A | 8/2000 | Jettka et al. |
| 6,133,223 | A | 10/2000 | Sampaio et al. |
| 6,217,851 | B1 | 4/2001 | Kleinberg et al. |
| 6,217,909 | B1 | 4/2001 | Sherwood et al. |
| 6,228,849 | B1 | 5/2001 | Thys-Jacobs |
| 6,248,335 | B1 | 6/2001 | Duan et al. |
| 6,251,439 | B1 | 6/2001 | Baron |
| 6,254,893 | B1 | 7/2001 | MacKeen |
| 6,274,544 | B1 | 8/2001 | Akkermans et al. |
| 6,287,599 | B1 | 9/2001 | Burnside et al. |
| 6,287,607 | B2 | 9/2001 | Pak et al. |
| 6,312,659 | B1 * | 11/2001 | Wise ............... 423/430 |
| 6,325,836 | B1 | 12/2001 | Wommack et al. |
| 6,368,638 | B1 | 4/2002 | Tiongson |
| 6,384,087 | B1 | 5/2002 | Zemel et al. |
| 6,395,301 | B1 | 5/2002 | Cantin |
| 6,413,291 | B1 | 7/2002 | Wommack et al. |
| 6,429,184 | B1 | 8/2002 | Akkerman et al. |
| 6,447,809 | B1 | 9/2002 | Krumhar et al. |
| 6,479,474 | B2 | 11/2002 | DeLuca et al. |
| 6,488,966 | B2 | 12/2002 | Baron |
| 6,492,024 | B1 | 12/2002 | Walter |
| 6,499,984 | B1 | 12/2002 | Ghebre-Sellassie et al. |
| 6,558,711 | B1 | 5/2003 | Baron |
| 6,635,278 | B1 | 10/2003 | Dahl et al. |
| 6,680,288 | B1 | 1/2004 | Groot et al. |
| 6,682,762 | B2 | 1/2004 | Register |
| 6,686,044 | B2 | 2/2004 | Nakai et al. |
| 6,716,454 | B2 | 4/2004 | Meignant et al. |
| 6,790,462 | B2 | 9/2004 | Hendricks |
| 6,808,700 | B2 | 10/2004 | Kiji et al. |
| 6,818,228 | B1 | 11/2004 | Walsdorf et al. |
| 6,936,087 | B2 | 8/2005 | Wommack et al. |
| 7,018,972 | B2 | 3/2006 | Akkerman et al. |
| 7,029,504 | B2 | 4/2006 | Rabie et al. |
| 7,029,703 | B2 | 4/2006 | Krumhar et al. |
| 7,053,038 | B2 | 5/2006 | Groot et al. |
| 7,198,653 | B2 * | 4/2007 | Lang et al. ............... 23/313 FB |

FOREIGN PATENT DOCUMENTS

JP    05-339171    12/1993

OTHER PUBLICATIONS

Fausett et al., "Evaluation of Quick Distintegrating Calcium Carbonate Tablets", AAPS Pharmscitech 2000, vol. 1, No. 3, 2000, pp. 1-7.
Database Internet, Data Sheet from 1-3, "Ground Calcium Carbonate", XP002483143, retrieved from Web-Archiv, <<http://web.archive.org/web/20020427071605/http://www.exportjamaica.org/jetco/click.htm>>, Apr. 27, 2002.
European Search Report for EP 04778146 dated Jun. 6, 2008.
U.S. Appl. No. 11/552,897, filed Oct. 25, 2006, Kevin W. Lang et al.
U.S. Appl. No. 11/552,901, filed Oct. 25, 2006, Kevin W. Lang et al.
U.S. Appl. No. 11/552,904, filed Oct. 25, 2006, Kevin W. Lang et al.
U.S. Appl. No. 11/675,436, filed Feb. 15, 2007, Kevin W. Lang et al.
Alfonso R. Gennaro, Remington: The Science and Practice of Pharmacy, vol. 2, 1615-1649 (19$^{th}$ ed. 1995).
Pformulate Excipients—Calcium Carbonate, http://www.pformulate.com/calcarb.htm, 2003.
Carrier Vibrating Equipment, Inc.—Fluid-Flow Vibrating Bed Systems, 1992, No. 16510.

* cited by examiner

CALCIUM CARBONATE GRANULATION

This application is a continuation application of U.S. application Ser. No. 10/631,923, filed Jul. 31, 2003, the entire contents of which are hereby incorporated by reference.

FIELD OF INVENTION

The present invention relates generally to highly compactable granulations and methods for preparing the same. More particularly, the present invention relates to highly compactable calcium carbonate granulations for use in pharmaceutical and nutraceutical tableting.

BACKGROUND OF THE INVENTION

Calcium is an essential nutrient and the most abundant mineral in the human body. Calcium plays a vital role in building healthy teeth and bones, blood clotting, muscle contraction, and nerve function. In addition to these benefits, it has recently been suggested that calcium reduces the risk of recurrence of colon polyps. see Baron J. A. et al. *New England Journal of Medicine* 1999; 340: 101-107. Most notably, calcium reduces the risk of bone loss caused by osteoporosis in both men and women. Despite these advantages, it has been estimated that half of all Americans do not consume sufficient amounts of calcium. More troubling, 80% of women, the group at highest risk for developing osteoporosis, do not consume enough calcium.

This deficiency is due in part to the large daily intake of calcium that is suggested by physicians. The United States Recommended Daily Allowance ("USRDA") of calcium for adults is 800 to 1,400 mg. The National Academy of Sciences, Institute of Medicine recommends calcium intakes of 1,200 mg per day for people over 50 years of age and 1,300 mg per day for people under 19 years of age. Not surprisingly, physicians recommend calcium supplements more than any other dietary supplement.

Commercial dietary calcium supplements are typically made from natural sources of calcium carbonate, including limestone and oyster shell. Since calcium carbonate contains only 40% by weight of elemental calcium, approximately 2.5 to 3.5 g of calcium carbonate must be consumed daily to meet the recommendations. It is not practical to make tablets containing such large amounts of calcium carbonate. Consequently, supplemental calcium regimens typically comprise administering two tablets daily of 500 to 600 mg of calcium. However, even at these calcium doses, most calcium tablets are very large and difficult or uncomfortable to swallow. This problem is exacerbated when excipients are also present in the formulation. As with any solid dose pharmaceutical or nutraceutical, large tablet size often leads to poor patient compliance. In addition to calcium supplements, this disadvantage is commonly encountered with tablets having large amounts of active ingredients, such as multi-vitamins and high-dose pharmaceuticals.

Prior approaches for reducing tablet size include increasing the compaction pressure during tableting and reducing the dose of some or all of the active ingredients in a tablet. There are disadvantages associated with both of these approaches. For instance, high compaction pressures during tableting may result in brittle tablets that are prone to breaking. Further, disintegration and dissolution characteristics of tablets may be affected by compaction pressure, altering the bioavailability of the active ingredient. Reducing the quantity of one or more active ingredients per tablet requires more tablets to be consumed to achieve a required dosage or, as in the case of some multi-vitamins, results in deficiencies of selected active ingredients. For example, most commercial multi-vitamin tablets provide only 10 to 20% of the USRDA recommended dose calcium. It is necessary to reduce the levels of calcium in these tablets in order to accommodate higher levels of other vitamins.

Calcium carbonate tablets, like other pharmaceutical and nutraceutical tablets, are prepared by the application of pressure to solid formulations. Some powdered formulations inherently possess the necessary cohesive and flow properties required for compression. Like most powders, however, calcium carbonate lacks the ability to be directly compressed and must be converted into a form more suitable for tableting through a process known as granulation.

Generally, the granulation process involves treating dry powders with agents that increase the adhesive properties of the particles resulting in stable agglomerations of the powder particles. Granulation methods known in the art include wet granulation, dry granulation, and fluid bed granulation. Of these, wet granulation is the most widely used method. In wet granulation, the dry powder components are blended in a suitable mixer followed by addition of a binding agent and further mixing to achieve the desired consistency. After drying, the granulated compositions typically have a free flowing, sand-like texture. Granulation provides the required cohesiveness and compactability for compression into tablets of satisfactory hardness and friability.

There is a continuing need for granulations that are highly compactable. Accordingly, it is an object of the invention to provide granulations that can be compressed into smaller tablets than those known heretofore. Further, it is an object of the invention to provide formulations and processes for preparing granulations.

SUMMARY OF THE INVENTION

In accordance with the foregoing objectives, highly compactable granulations and methods for preparing highly compactable granulations are provided. When compressed into tablets, these granulations provide tablets having small sizes or volumes heretofore not achievable in the art. In the preferred practice of the present invention, calcium carbonate granulations are provided. While the following embodiments and examples relate to the preferred calcium carbonate granulations, it should be understood that the methods of the present invention would be useful for granulation of any powdered material. Accordingly, any granulation made according to the methods or formulations disclosed herein is contemplated to be within the scope of the present invention.

It has surprisingly been found that highly compactable calcium carbonate granulations are provided by mixing a composition comprising calcium carbonate in a mixer capable of creating high shear and drying the composition in a convection drying oven. Additional improvements in compactability are obtained by employing formulations comprising powdered compositions of small median particle size. Further improvements are obtained by employing formulations comprising two or more powdered compositions of differing median particle size. While the benefits of the present invention are most fully realized when these formulations are used in conjunction with the granulation process of the present invention, the invention is not so limited. It is contemplated that the present formulations will provide improved granulations when used in conjunction with any prior art granulation processes.

In one aspect of the present invention, granulations are provided comprising powdered materials having a median particle diameter of about 0.1 to about 20 micrometers ("μm"). Preferred granulations according to this embodiment have median particle diameters of about 1 to about 15 μm.

In another aspect of the present invention, granulated compositions comprising a first calcium carbonate composition having a median particle diameter from about 10 to about 25 μm and a second calcium carbonate composition having a median particle diameter from about 0.1 to about 10 μm are provided. In a preferred embodiment, the first calcium carbonate composition has a median particle diameter from about 12 to about 17 μm and the second calcium carbonate composition has a median particle diameter from about 1 to about 5 μm.

In another aspect of the invention, granulated compositions comprising a first calcium carbonate composition having a median particle diameter from about 10 to about 25 μm; a second calcium carbonate composition having a median particle diameter from about 1 to about 10 μm; and a third calcium carbonate composition having a median particle diameter from about 0.1 to about 1 μm are provided.

Yet another aspect of the present invention provides a granulation process comprising the steps of mixing a powdered composition in a mixer capable of creating high shear and drying the composition in a convection oven. A preferred embodiment of the process according to this aspect of the invention comprises the steps of: (1) mixing powdered calcium carbonate, maltodextrin and optionally additional excipients in a mixer capable of creating high shear; (2) adding water to the composition and mixing; (3) adding oil to the composition and mixing; and (4) drying the resulting composition in a convection drying oven.

An additional aspect of the invention provides high density calcium carbonate granulations. In this regard, granulated calcium carbonate compositions having an average tap density between about 0.9 and about 2.0 g/cm³ are provided. Preferred granulated calcium carbonate compositions are provided having an average tap density between about 1.1 and about 2.0 g/cm³. The most preferred granulated calcium carbonate compositions according to the invention have tap densities greater than 1.3 g/cm³.

A further aspect of the invention provides tablets comprising the disclosed granulations. Tablets prepared from the granulations of the invention have densities about 20% to about 35% greater than commercially available calcium supplement tablets. Accordingly, the volume of the tablets prepared from the granulations of the invention is about 20% to about 35% less than the volume of commercially available calcium supplement tablets.

These and other aspects of the invention may be more clearly understood by reference to the following detailed description of the invention and the appended claims.

DETAILED DESCRIPTION OF THE INVENTION

In the following description of the invention, it is to be understood that the terms used have their ordinary and accustomed meanings in the art, unless otherwise specified. As used herein, the term "granulation" refers to free-flowing compositions having sufficient cohesive properties for compression into tablets. The term "granulation process" includes, but is not limited to those processes known in the art as wet granulation, dry granulation, fluid-bed granulation, agglomeration and spheronization.

1. Granulation Compositions.

One aspect of the present invention provides highly dense and highly compactable granulation compositions. In the preferred practice of the invention, the granulation compositions comprise calcium carbonate.

It is well known in the art that calcium carbonate powders having a variety of median particle diameters are commercially available. For example, food grade and USP grade calcium carbonate powders having median particle diameters ranging from 0.7 to 20 μm are available from suppliers such as OMYA, Inc. (Alpharetta, Ga.), J.M Huber Corp. (Atlanta, Ga.), and Minerals Technologies Inc. (New York, N.Y.).

As shown in Table 1, calcium carbonate powders having larger median particle diameters provide more dense compositions when directly compressed than calcium carbonate powders having smaller median particle diameters.

TABLE 1

| Calcium Product[1] | Median Diameter (μm) | Packed Density (g/cm³) | Calcium Product[2] | Median Diameter (μm) | Packed Density (g/cm³) |
|---|---|---|---|---|---|
| OMYA-Cal FG-4 AZ | 3.5 | 1.10 | HuberCAL ® 150FG | 4 | 1.2 |
| OMYA-Cal FG-6 AZ | 6.0 | 1.20 | HuberCAL ® 250FG | 6 | 1.3 |
| OMYA-Cal FG-10 AZ | 12 | 1.50 | HuberCAL ® 500FG | 12 | 1.5 |
| OMYA-Cal FG-15 AZ | 15 | 1.55 | HuberCAL ® 850FG | 20 | 1.6 |

[1]Available from OMYA, Inc.;
[2]Available from J. M Huber Corp.

Based on the relationship between particle size and density, the skilled artisan would be motivated to select calcium carbonate powders of large median particle size in attempts to provide highly dense and highly compactable granulations. It has surprisingly been found, however, that granulated compositions comprising small median particle size calcium carbonate powders, which alone have relatively low pack densities, possess improved compactability as compared to granulated compositions consisting of larger median particle size calcium carbonate powders. Accordingly, granulated compositions comprising small median particle size calcium carbonate powders provide unexpectedly small tablets upon compression.

In one embodiment of the present invention, calcium carbonate granulations are provided comprising powdered calcium carbonate having a median particle diameter of about 0.1 to about 20 μm. Within this range, exemplary granulations comprise calcium carbonate having median particle diameters of about 3.5, 6, and 12 μm. In a preferred embodiment, the granulated compositions comprise calcium carbonate having a median particle diameter between about 10 and about 12 μm. The granulated compositions of the invention may further comprise other ingredients including but not limited to maltodextrin, gum acacia, oil and water.

In the practice of the invention, it has been found desirable to employ powdered compositions having narrow particle diameter distributions about the mean. It will be recognized that the term "narrow particle diameter distributions" cannot generally be quantified since the variance in particle size is related to the median particle diameter of a powder. Additionally, manufacturing limitations associated with each median particle size powder affect the distribution about the mean. It is within the skill in the art to select powders with narrow median particle sizes.

As used herein, calcium carbonate powders having a median particle size of 15 µm have narrow particle diameter distributions if about 65% or more of the bulk volume of the powder has a particle size between 5 and 25 µm (±66% from the median) and about 40% or more of the bulk volume has a particle size between about 10 and 20 µm (±33% from the median). Similarly, calcium carbonate powders having a median particle size of 12 µm have narrow particle diameter distributions if about 50% or more of the bulk volume of the powder has a particle size between 4 and 20 µm (±66% from the median) and about 30% or more of the bulk volume has a particle size between about 8 and 16 µm (±33% from the median). Calcium carbonate powders having a median particle size of 6 µm have narrow particle diameter distributions if about 55% or more of the bulk volume of the powder has a particle size between 2 and 10 µm (±66% from the median) and about 25% or more of the bulk volume has a particle size between about 4 and 8 µm (±33% from the median). Calcium carbonate powders having a median particle size of 3-4 µm have narrow particle diameter distributions if about 50% or more of the bulk volume of the powder has a particle size between 1.2 and 5.8 µm (±66% from the median) and about 25% or more of the bulk volume has a particle size between about 2.3 and 4.7 µm (±33% from the median). Suitable calcium carbonate powders with narrow particle diameter distributions include, but are not limited to those available from OMYA, Inc. under the trademarks OMYA-Cal FG 15, OMYA-Cal USP 15, OMYA-Cal LL OC FG 15 BTH, OMYA-Cal LL USP 15, OMYA-Cal LL USP 15 BTH, OMYA-Cal FG-10AZ, OMYA-Cal FG-6AZ, and OMYA-Cal USP-4AZ.

While the preferred powders have narrow median particle size distributions it will be understood that any powder is contemplated as being useful with the present invention. For example, 12 µm median particle size calcium carbonate powders having a distribution about the median broader than described above provide granulations superior in compactability to those of the prior art.

In the practice of the invention, it has also been found useful to employ small median particle size powders in combination with larger median particle size powders. In one embodiment of the invention, the granulation compositions comprise a first powdered composition having a median particle diameter from about 10 to about 25 µm and a second powdered composition having a median particle diameter from about 0.1 to about 10 µm.

The first and second powdered compositions may be any powdered material. Preferably, the first and second powdered compositions are materials used in the formulation of pharmaceutical and nutraceutical tablets, including active ingredients and excipients. Examples of powdered materials and excipients contemplated to be useful according to the present invention include but are not limited to calcium carbonate, dicalcium phosphate, calcium sulfate, ferrous sulfate and other iron compounds, lactose, cellulose, micro-crystalline cellulose (Avicel), kaolin, mannitol, maltodextrin, oil, sodium chloride, starch, powdered sugar, talc (magnesium silicate hydroxide), and silica. In the preferred practice of the invention the first and second powdered compositions are calcium carbonate.

In a preferred embodiment of the invention, the first powdered composition comprises calcium carbonate having a median particle diameter of about 12 to about 17 µm and the second powdered composition comprises calcium carbonate having a median particle diameter of about 1 to about 5 µm. In a more preferred embodiment of the invention, the first powdered composition comprises calcium carbonate having a median particle diameter of about 15 µm and the second powdered composition comprises calcium carbonate having a median particle diameter of about 4 µm.

The first and second powdered compositions may each comprise any weight % of the granulated composition. In a preferred embodiment, the first powdered composition comprises from about 50 to about 100 weight % of the granulated composition and the second powdered composition comprises from about 0 to about 50 weight % of the granulated composition. In a more preferred embodiment, the first powdered composition comprises from about 60 to about 80 weight % of the granulated composition and the second powdered composition comprises from about 20 to about 40 weight % of the granulated composition. In the most preferred embodiment, the first powdered composition comprises about 70 weight % of the granulated composition and the second powdered composition comprises about 30 weight % of the granulated composition.

It will be understood that the first and second powdered compositions according to the invention are not necessarily the same chemical compound. For instance, it is contemplated that the first powdered composition may be an excipient and the second powdered composition may be an active ingredient, or vice versa. In one embodiment of the invention, the first powdered composition is calcium carbonate and the second powdered composition is talc.

Another granulated composition according to the present invention comprises a first powdered composition having a median particle diameter from about 10 to about 20 µm, a second powdered composition having a median particle diameter from about 1 to about 10 µm, and a third powdered composition having a median particle diameter from about 0.1 to about 1 µm. The first, second, and third powdered compositions may each comprise any weight % of granulated composition. In a preferred embodiment, the granulated composition comprises from about 60 to about 80 weight % of the first powdered composition, from about 20 to about 40 weight % of the second powdered composition, and from about 0.5 to about 5 weight % of the third powdered composition.

The first, second and third powdered compositions may be independently selected from any powdered material. In a preferred embodiment, at least one of the first, second, and third powdered compositions is calcium carbonate. In a more preferred embodiment, each of the first, second, and third powdered compositions are calcium carbonate.

The granulated compositions of the present invention may comprise other materials in addition to the powdered compositions described above. For example, it may be desirable to add excipients to the granulation to impart certain physical characteristics to the granulation or resulting tablets. Excipients that may be used with the present invention include, but are not limited to diluents, binders, glidants, lubricants, disintegrants, colors, flavors, sweeteners, and solubility retarding agents. Preferred excipients according to the invention are maltodextrin and oil. When present, the granulated compositions preferably comprise between about 2 and about 10 weight % maltodextrin and about 0.1 to about 1 weight % oil.

It is contemplated that any oil or oil-like material compatible with a pharmaceutical or nutraceutical product will be useful according to the invention. Preferred oils are canola oil, mineral oil, coconut oil, cotton seed oil, rape seed oil, sunflower seed oil, palm oil, vegetable oil and soy oil. Mineral oil is the most preferred oil according to the invention.

The formulations may further comprise one or more hydrocolloids. Any hydrocolloid that is compatible with a pharmaceutical or nutraceutical product may be used in the granulations of the invention. Preferred hydrocolloids are selected from vegetable gums, including but not limited to alginates, carrageenan, dextran, furcellaran, pectin, gelatin, gum agar, locust bean gum, gum ghatti, guar gum, gum tragacanth, acacia, gum arabic, xanthan gum, karaya gum, tara gum, cellulose derivatives, starch derivatives, and combinations thereof. One vegetable gum that has been found to be particularly useful is gum acacia.

The granulated calcium carbonate compositions of the present invention have a free-flowing quality and a dense, sand-like texture. Preferred granulations have an average tap density between about 0.9 and about 2.0 g/cm$^3$ as measured using a Van Kel bulk and tap density gauge. More preferably, the granulated compositions have an average density between about 1.1 and about 2.0 g/cm$^3$. Most preferred granulated compositions according to the invention have an average density between about 1.3 and about 2.0 g/cm$^3$.

2. Granulation Process.

Another aspect of the present invention provides a process for preparing highly dense and highly compressible granulation compositions.

The granulation process of the present invention comprises the steps of: (1) mixing a powdered material and optionally additional ingredients such as excipients in a mixer capable of creating high shear; and (2) drying the resulting composition in a convection drying oven.

A preferred embodiment of the process comprises the steps of: (1) mixing powdered calcium carbonate, maltodextrin and optionally additional excipients in a mixer capable of creating high shear; (2) adding water to the composition and mixing therewith; (3) adding oil to the composition and mixing therewith; (4) drying the resulting composition in a convection drying oven. The amount of calcium carbonate, maltodextrin, and oil are determined according the proportions described above. The amount of water added will preferably be between about 5 and about 20 weight % based on the amount of calcium carbonate. However, the amount of water may be more or less depending on the desired density and texture of the granulation. In the practice of the invention it has been found desirable to use hot water or steam. Preferably, the water is heated to about 93° C. or greater before it is mixed with the calcium carbonate. After the composition is mixed with water, the composition will preferably reach a temperature of about 45° C. to about 50° C.

A more preferred embodiment of the process comprises the steps of: (1) mixing at least two powdered calcium carbonate compositions having differing median particle size distribution, as described above, with maltodextrin and optionally additional excipients in a mixer capable of creating high shear; (2) mixing for about 60 seconds at mixer speeds from about 200 rpm to about 300 rpm; (3) adding an amount of hot water or steam comprising from about 5 to about 20 weight % based on the total amount of calcium carbonate composition; (4) mixing for about 6 minutes; (5) adding oil or oil-like material to the composition and mixing therewith; and (6) drying the resulting composition in a convection drying oven.

While the granulated compositions may be dried by any method known in the art, the compositions are preferably dried in a convection oven. Examples of convection drying ovens include, but are not limited to, tray dryers, vertical fluidized bed ovens, horizontal fluidized bed ovens, spray dryers, and impingement ovens. It has been found useful to adjust the oven conditions to yield a final composition having a water content of less than approximately 1% by weight. In the preferred practice of the invention, the composition is heated to between about 50° C. to about 150° C. in the oven.

It will be understood that the mixing times described above will vary somewhat depending on factors such as the total quantity of materials to be mixed, the speed of the mixer, and the design of the impeller blades. It is within the skill in the art to optimize the mixing times to achieve the desired texture and density of the resulting granulation.

It is contemplated that any mixer which provides high shear may be employed in the process, including but not limited to Hobart mixers and those mixers known in the art as "high shear" mixers.

It will be understood that the processes described herein have general applicability for preparing highly dense and highly compressible granulated compositions and are not limited to granulating the formulations described above. Similarly, it is contemplated that the formulations described herein will provide improved granulated compositions when employed in any granulation process known in the art, including but not limited to fluidized bed granulation processes.

The granulations disclosed herein are useful for preparing pharmaceutical and nutraceutical tablets. Tablets according to the present invention include but are not limited to molded tablets, chewable tablets, pellets, pills, triturates, hypodermic tablets, effervescent tablets, controlled-release tablets, and immediate release tablets. Tablets prepared from the granulations of the invention have densities about 20% to at least about 35% greater than commercially available calcium supplement tablets. Accordingly, the volume of the tablets prepared from the granulations of the invention is about 20% to at lest about 35% less than the volume of commercially available calcium supplement tablets.

EXAMPLE I

A granulated calcium carbonate composition was prepared from calcium carbonate having a median particle diameter of about 6 μm using the process of the present invention. The ingredients for this formulation are listed in Table 2.

TABLE 2

| Ingredient | Weight Kg |
| --- | --- |
| OMYA-CAL FG-6AZ[1] | 22.70 |
| Maltrin M100/Maltodextrin[2] | 1.20 |
| Drakeol 34/Mineral Oil[3] | 0.24 |
| Purified Water | 3.00 |

[1]OMYA, Inc.;
[2]Grain Processing Corp.;
[3]Penreco.

The bowl of a Collette Gral Model 600 high shear mixer was charged with calcium carbonate (OMYA-CAL FG-6AZ) and maltodextrin (Maltrin M100) in the amounts shown in Table 1. These ingredients were mixed for 60 seconds at mixer speed from about 200 to about 300 rpm. Purified water heated to approximately 93° C. was then added to the mixture through a water line. The composition was mixed until steam stopped being produced from the composition (approximately six minutes). Mineral oil was then sprayed onto the composition using a spray nozzle fed by a line through the head of the mixer. The composition was mixed for approximately one minute.

The mixing bowl was then lowered and the composition was collected in a plastic bag. The composition was then poured through a transition funnel into a vibratory feeder which deposited the charge onto a belt conveyor. The belt conveyor conveyed the composition onto a weigh belt that metered the composition uniformly into a Carrier model QAD/C 1260 S horizontal fluidized bed convection oven. The oven temperature was controlled to produce a product temperature of about 100° C. to about 150° C. The composition exiting the terminal end of the oven had a moisture content of less than about 1% by weight.

The dry composition was screened using an 18×18 U.S. mesh screen and the particles passing therethrough were collected as a first batch. The oversize particles remaining on the screen were collected and passed through a Crack-U-Lator roll granulator in order to reduce the size of oversized particles. The discharge from the Crack-U-Lator was then passed through an 18×18 U.S. mesh screen and combined with the first batch.

The granulated composition was free flowing and had a sand-like texture. The composition had an improved mouthfeel and reduced "chalkiness" as compared to powdered calcium carbonate.

The tap density of the resulting dry granulation was measured using a Van Kel Bulk and Tap Density Gauge. The tap density of the calcium carbonate granulation was greater than or equal to about 1.1 g/cm$^3$. Tablets containing 600 mg of calcium carbonate prepared from this granulation were about 20% smaller in volume than commercially available 600 mg Caltrate® tablets.

EXAMPLE II

To further investigate the effect of median particle diameter on granulation density, a granulated composition was prepared from calcium carbonate powder having a median particle diameter of about 10 μm (OMYA-CAL FG-10AZ) using the process of the present invention. The ingredients for this formulation are listed in Table 3.

TABLE 3

| Ingredient | Weight Kg |
| --- | --- |
| OMYA-CAL FG-10AZ[1] | 22.70 |
| Maltrin M100/Maltodextrin[2] | 1.20 |
| Drakeol 34/Mineral Oil[3] | 0.24 |
| Purified Water | 3.00 |

[1]OMYA, Inc.;
[2]Grain Processing Corp.;
[3]Penreco.

The granulation process was identical to the process described in Example 1.

The tap density of the resulting dry granulation was measured using a Van Kel Bulk and Tap Density Gauge. The tap density of the calcium carbonate granulation was greater than or equal to about 1.0 g/cm$^3$. Tablets containing 600 mg of calcium carbonate prepared from this granulation were about 20% smaller in volume than commercially available 600 mg Caltrate® tablets.

EXAMPLE III

A granulated composition was prepared from calcium carbonate having a median particle diameter of about 15 μm (Calcium Carbonate LL USP 15, OMYA, Inc.) using the process of the present invention. The ingredients for this formulation are listed in Table 4.

TABLE 4

| Ingredient | Weight % |
| --- | --- |
| Calcium Carbonate LL USP 15[1] | 93.21 |
| Maltrin M-180/Maltodextrin[2] | 6.58 |
| Drakoel 34/Mineral Oil[3] | 0.205 |

TABLE 4-continued

| Ingredient | Weight % |
| --- | --- |
| Hydroxypropyl Methylcellulose[4] | 0.001 |
| Stearic Acid | 0.001 |
| Polyplasdone XL/Crospovidone[5] | 0.001 |
| Magnesium Stearate | 0.001 |

[1]OMYA, Inc.;
[2]Grain Processing Corp.;
[3]Penreco;
[4]Dow Chemical Co.;
[5]International Specialty Products, Inc.

The granulation process was identical to the process described in Example 1.

The tap density of the resulting dry granulation was measured using a Van Kel Bulk and Tap Density Gauge. The tap density of the calcium carbonate granulation was greater than or equal to about 1.0 g/cm$^3$. Tablets containing 600 mg of calcium carbonate prepared from this granulation were about 20% smaller in volume than commercially available 600 mg Caltrate® tablets.

EXAMPLE IV

This example illustrates the improvement in density that is achieved by employing a formulation comprising two calcium carbonate compositions having differing median particle diameters in the process of the present invention. As shown in Table 5, the composition comprises a 50:50 weight ratio of calcium carbonate having a median particle diameter of about 15 μm (Cal Carb OC USP PDR) and calcium carbonate having a median particle diameter of about 6 μm (OMYA-CAL FG-6AZ).

TABLE 5

| Ingredient | Weight Kg |
| --- | --- |
| OMYA-CAL FG-6AZ[1] | 11.35 |
| Cal Carb OC USP PDR[1] | 11.35 |
| Maltrin M100/Maltodextrin[2] | 1.20 |
| Drakeol 34/Mineral Oil[3] | 0.24 |
| Purified Water | 3.00 |

[1]OMYA, Inc.;
[2]Grain Processing Corp.;
[3]Penreco.

The granulation process was identical to the process described in Example 1.

The tap density of the resulting dry granulation was measured using a Van Kel Bulk and Tap Density Gauge. The tap density of the calcium carbonate granulation was greater than or equal to about 1.1 g/cm$^3$. Tablets containing 600 mg of calcium carbonate prepared from this granulation were about 20% smaller in volume than commercially available 600 mg Caltrate® tablets.

EXAMPLE V

This Example provides a granulated composition comprising a 70:30 weight ratio of calcium carbonate having a median particle diameter of about 15 μm (Cal Carb OC USP PDR) and calcium carbonate having a median particle diameter of about 4 μm (OMYA-CAL USP-4AZ).

TABLE 6

| Ingredient | Weight Kg |
|---|---|
| OMYA-CAL USP-4AZ[1] | 6.80 |
| Cal Carb OC USP PDR[1] | 15.9 |
| Maltrin M100/Maltodextrin[2] | 1.20 |
| Drakeol 34/Mineral Oil[3] | 0.24 |
| Purified Water | 3.00 |

[1]OMYA, Inc.;
[2]Grain Processing Corp.;
[3]Penreco.

The granulation process was identical to the process described in Example 1.

The bulk density of the granulation was about 0.9 g/cm$^3$. The tap density of the resulting dry granulation was measured using a Van Kel Bulk and Tap Density Gauge. The tap density of the calcium carbonate granulation was greater than or equal to about 1.1 g/cm$^3$. Tablets containing 600 mg of calcium carbonate prepared from this granulation were about 20% smaller in volume than commercially available 600 mg Caltrate® tablets.

EXAMPLE VI

This Example provides a granulated composition comprising calcium carbonate having a median particle diameter of about 10 μm with a broad particle size distribution about the median.

TABLE 7

| Ingredient | Weight % |
|---|---|
| Calcium Carbonate OC-10[1] | 94.04 |
| Maltrin M100/Maltodextrin[2] | 4.97 |
| Drakeol 34/Mineral Oil[3] | 0.99 |

[1]OMYA, Inc.;
[2]Grain Processing Corp.;
[3]Penreco.

The granulation process was identical to the process described in Example 1, with an amount of hot water equal to about 10% by weight based on the weight of calcium carbonate added during mixing.

The tap density of the resulting dry granulation was measured using a Van Kel Bulk and Tap Density Gauge. The tap density of the calcium carbonate granulation was between about 1.25 and 1.31 g/cm$^3$. Tablets containing 600 mg of calcium carbonate prepared from this granulation were about 20% smaller in volume than commercially available 600 mg Caltrate® tablets.

The invention having been described by the foregoing description of the preferred embodiments, it will be understood that the skilled artisan may make modifications and variations of these embodiments without departing from the spirit or scope of the invention as set forth in the following claims:

We claim:

1. A process for preparing a calcium carbonate granulation comprising the steps of:
   (a) mixing, in a mixer capable of creating high shear, a composition comprising:
      (i) calcium carbonate powder having a median particle diameter between about 10 to about 12 μm;
      (ii) between about 5 to 20% by weight water based on the weight of said calcium carbonate powder; and
      (iii) one or more excipients selected from the group consisting of diluents, binders, glidants, lubricants, disintegrants, colors, flavors, sweeteners, solubility retarding agents, and combinations thereof; and
   (b) drying the composition to a water content of less than about 1% by weight in a drier selected from the group consisting of a tray dryer, a vertical fluidized bed oven, a horizontal fluidized bed oven, a spray dryer, and an impingement oven; to provide a calcium carbonate granulation having sufficient cohesiveness and compactability for compression into pharmaceutical or nutraceutical supplement tablets.

2. The process of claim 1 wherein said calcium carbonate powder has a median particle diameter of about 12 μm.

3. The process of claim 2 wherein said calcium carbonate powder has a particle size distribution wherein at least about 50% of the bulk volume of the powder has a particle size between 4 and 20 microns and at least about 30% of the bulk volume of the powder has a particle size between about 8 and 16 microns.

4. The process of claim 2 wherein said calcium carbonate powder has a particle size distribution broader than a distribution wherein at least about 50% of the bulk volume of the powder has a particle size between 4 and 20 microns and at least about 30% of the bulk volume of the powder has a particle size between about 8 and 16 microns.

5. The process of claim 1, wherein said drier is a tray dryer.

6. The process of claim 1, wherein said drier is a vertical fluidized bed oven.

7. The process of claim 1, wherein said drier is a horizontal fluidized bed oven.

8. The process of claim 1, wherein said drier is a spray dryer.

9. The process of claim 1, wherein said drier is an impingement oven.

10. The process of claim 1, wherein said mixer capable of creating high shear is a high shear mixer.

11. The process of claim 1, wherein the tap density of said calcium carbonate granulation is between about 0.9 and about 2.0 g/cm$^3$.

12. The process of claim 1, wherein the tap density of said calcium carbonate granulation is between about 1.1 and about 2.0 g/cm$^3$.

13. The process of claim 1, wherein the tap density of said calcium carbonate granulation is between about 1.3 and about 2.0 g/cm$^3$.

14. The process of claim 1, wherein said composition includes a binder.

15. The process of claim 14, wherein said binder includes maltodextrin.

16. The process of claim 15, wherein said maltodextrin comprises from about 2 to about 10% by weight of said calcium carbonate granulation.

17. The process of claim 1, wherein said composition includes oil.

18. The process of claim 17, wherein said oil comprises from about 0.1 to about 1% by weight of said calcium carbonate granulation.

19. The process of claim 1, wherein said composition includes gum acacia.

* * * * *